(12) United States Patent
Hoffman et al.

(10) Patent No.: US 12,121,649 B2
(45) Date of Patent: Oct. 22, 2024

(54) CARTRIDGE FOR AN AUTOMATED AEROSOL DISPENSING DEVICE

(71) Applicant: Ecological Balancing Technologies Corporation, Wilmington, DE (US)

(72) Inventors: Michael Hoffman, Moshav Udim (IL); Yuli Horesh, Tel-Aviv (IL); Pini Pinhas Gross, Yavne (IL)

(73) Assignee: Ecological Balancing Technologies Corporation, Wilmington, DE (US)

( * ) Notice: Subject to any disclaimer, the term of this patent is extended or adjusted under 35 U.S.C. 154(b) by 913 days.

(21) Appl. No.: 16/980,394

(22) PCT Filed: Mar. 12, 2019

(86) PCT No.: PCT/IB2019/052008
§ 371 (c)(1),
(2) Date: Sep. 13, 2020

(87) PCT Pub. No.: WO2019/175775
PCT Pub. Date: Sep. 19, 2019

(65) Prior Publication Data
US 2021/0046256 A1 Feb. 18, 2021

Related U.S. Application Data

(60) Provisional application No. 62/641,441, filed on Mar. 12, 2018.

(51) Int. Cl.
*A61M 11/00* (2006.01)
*A61L 9/14* (2006.01)
(Continued)

(52) U.S. Cl.
CPC .............. *A61M 11/00* (2013.01); *A61L 9/14* (2013.01); *A61M 39/10* (2013.01);
(Continued)

(58) Field of Classification Search
CPC ............. A61M 11/00; A61M 39/10; A61M 2039/1077; A61M 2205/3327;
(Continued)

(56) References Cited

U.S. PATENT DOCUMENTS

| 2,293,722 A | 8/1942 | Erickson |
| D221,836 S | 9/1971 | Giles et al. |

(Continued)

FOREIGN PATENT DOCUMENTS

| CN | 1177636 | 4/1998 |
| CN | 1642827 | 7/2005 |

(Continued)

OTHER PUBLICATIONS

Official Action Dated May 26, 2022 from US Patent and Trademark Office Re. U.S. Appl. No. 17/019,596. (46 pages).

(Continued)

*Primary Examiner* — Michael R Reid
*Assistant Examiner* — Tina Zhang

(57) ABSTRACT

A connector configured to support a nebulizer inside a cartridge includes an annular wall, a conduit, and a plurality of spokes between the annular wall and the conduit. The spokes define openings therebetween and the annular wall is shaped and sized to be fitted into a lip of a bottle. A cartridge includes a housing configured to house a liquid, a collar defining an opening into the cartridge, the connector and a nebulizer held within the housing with the connector. Optionally, an anti-spill cover is fitted in an outlet of the cartridge.

4 Claims, 16 Drawing Sheets

(51) Int. Cl.
*A61M 39/10* (2006.01)
*B05B 11/00* (2023.01)
*B05B 17/06* (2006.01)

(52) U.S. Cl.
CPC ...... *B05B 11/0054* (2013.01); *B05B 17/0676* (2013.01); *A61L 2209/133* (2013.01); *A61L 2209/134* (2013.01); *A61M 2039/1077* (2013.01); *A61M 2205/3327* (2013.01)

(58) Field of Classification Search
CPC .. A61M 15/009; A61L 9/14; A61L 2209/133; A61L 2209/134; B05B 11/0054; B05B 17/0676; B05B 7/2424; B05B 17/06; B05B 11/028; B05B 11/06; B01F 27/80
See application file for complete search history.

(56) References Cited

U.S. PATENT DOCUMENTS

| | | | |
|---|---|---|---|
| 3,675,832 A * | 7/1972 | Ruscitti | B65D 83/48 222/402.24 |
| D239,922 S | 5/1976 | Utley | |
| D250,394 S | 11/1978 | Menius | |
| 4,164,055 A | 8/1979 | Townsend | |
| 4,245,788 A * | 1/1981 | Wright | B05B 11/0059 222/206 |
| D279,452 S | 7/1985 | Beechuk | |
| D284,362 S | 6/1986 | Biesecker | |
| D309,711 S | 8/1990 | Biesecker | |
| D376,760 S | 12/1996 | Sykes | |
| D433,336 S | 11/2000 | Weber | |
| 6,405,944 B1 | 6/2002 | Benalikhoudja | |
| D472,471 S | 4/2003 | McClure et al. | |
| D473,143 S | 4/2003 | McClure et al. | |
| D449,992 S | 5/2004 | Brauner et al. | |
| D571,662 S | 6/2008 | Clark et al. | |
| 7,858,336 B1 | 12/2010 | Garner et al. | |
| D630,946 S | 1/2011 | Crawford | |
| D656,599 S | 3/2012 | Browder | |
| D663,215 S | 7/2012 | Clay et al. | |
| D667,101 S | 9/2012 | Browder | |
| D673,253 S | 12/2012 | Mack | |
| D678,496 S | 3/2013 | Browder | |
| 8,986,610 B2 | 3/2015 | Ben Haim | |
| 9,486,552 B1 | 11/2016 | Ansley et al. | |
| 9,573,750 B2 * | 2/2017 | Seling | B65D 83/38 |
| D805,909 S | 12/2017 | Matsuishi | |
| D875,532 S | 2/2020 | Lehanneur | |
| D879,613 S | 3/2020 | Lehanneur | |
| 10,814,028 B2 | 10/2020 | Becker | |
| 2002/0042965 A1 | 4/2002 | Salem et al. | |
| 2003/0189066 A1 | 10/2003 | Schiller | |
| 2004/0221415 A1 | 11/2004 | Tondra et al. | |
| 2005/0160553 A1 | 7/2005 | Gregory | |
| 2005/0252930 A1 | 11/2005 | Contadini et al. | |
| 2007/0217945 A1 | 9/2007 | Selander | |
| 2008/0216273 A1 | 9/2008 | Medema et al. | |
| 2009/0238716 A1 | 9/2009 | Weening | |
| 2009/0265876 A1 | 10/2009 | Gardner et al. | |
| 2009/0324815 A1 | 12/2009 | Nielsen et al. | |
| 2010/0021576 A1 | 1/2010 | Chang et al. | |
| 2011/0214245 A1 | 9/2011 | Bassett | |
| 2012/0152882 A1 | 6/2012 | Tune | |
| 2012/0168971 A1 | 7/2012 | Hansen et al. | |
| 2013/0015956 A1 | 1/2013 | Wegelin et al. | |
| 2013/0068783 A1 | 3/2013 | Gasper et al. | |
| 2014/0007866 A1 * | 1/2014 | Yuki | A61M 11/02 128/200.21 |
| 2014/0263426 A1 | 9/2014 | Gasper | |
| 2016/0073844 A1 | 3/2016 | Park | |
| 2016/0101925 A1 | 4/2016 | Franz et al. | |
| 2016/0183538 A1 | 6/2016 | Taghavi et al. | |
| 2016/0325055 A1 * | 11/2016 | Cameron | A24F 40/50 |
| 2017/0000305 A1 | 1/2017 | Gordon et al. | |
| 2017/0035262 A1 | 2/2017 | Li et al. | |
| 2017/0035925 A1 | 2/2017 | Sevy | |
| 2017/0348364 A1 | 12/2017 | Garner et al. | |
| 2018/0368312 A1 | 12/2018 | Strang | |
| 2020/0405781 A1 | 12/2020 | Holzapfel et al. | |
| 2020/0407807 A1 | 12/2020 | Holzapfel et al. | |
| 2020/0407808 A1 | 12/2020 | Holzapfel et al. | |
| 2020/0407809 A1 | 12/2020 | Holzapfel et al. | |
| 2021/0046497 A1 | 2/2021 | Hoffman et al. | |
| 2021/0204774 A1 | 7/2021 | Dery et al. | |

FOREIGN PATENT DOCUMENTS

| | | | |
|---|---|---|---|
| CN | 1934241 | | 3/2007 |
| CN | 103589655 | | 2/2014 |
| CN | 103703121 | | 4/2014 |
| CN | 104487566 | | 4/2015 |
| CN | 104688895 | | 6/2015 |
| CN | 104736162 | | 6/2015 |
| CN | 204501790 | | 7/2015 |
| CN | 204501790 U | * | 7/2015 |
| CN | 303340433 S | | 8/2015 |
| CN | 105087423 | | 11/2015 |
| CN | 105219669 | | 1/2016 |
| CN | 205032305 | | 2/2016 |
| CN | 107567493 | | 1/2018 |
| CN | 107723267 | | 2/2018 |
| KR | 20-2009-0007893 | | 8/2009 |
| KR | 10-2014-0128870 | | 11/2014 |
| KR | 10-2017-0130341 | | 11/2017 |
| WO | WO 01/34182 | | 5/2001 |
| WO | WO 2016/060934 | | 4/2016 |
| WO | WO 2016/118850 | | 7/2016 |
| WO | WO 2016/118864 | | 7/2016 |
| WO | WO 2019/175774 | | 9/2019 |
| WO | WO 2019/175775 | | 9/2019 |
| WO | WO 2019/175777 | | 9/2019 |
| WO | WO 2019/175777 A8 | | 9/2019 |
| WO | WO 2019/175780 | | 9/2019 |
| WO | WO 2019/175782 | | 9/2019 |
| WO | WO 2019/175782 A8 | | 9/2019 |
| WO | WO 2019/175783 | | 9/2019 |
| WO | WO 2019/224691 | | 11/2019 |
| WO | WO 2019/175783 A8 | | 10/2020 |

OTHER PUBLICATIONS

Notice of Allowance Dated Mar. 4, 2022 From the US Patent and Trademark Office Re. U.S. Appl. No. 17/019,280. (7 Pages).
Restriction Official Action Dated Mar. 4, 2022 From the US Patent and Trademark Office Re. U.S. Appl. No. 17/019,596. (10 Pages).
Notice of Allowance Dated Mar. 24, 2022 from US Patent and Trademark Office Re. U.S. Appl. No. 17/019,280. (4 pages).
Official Action Dated Sep. 7, 2023 from the US Patent and Trademark Office Re. U.S. Appl. No. 17/057,727. (53 pages).
International Preliminary Report on Patentability Dated Dec. 3, 2020 From the International Bureau of WIPO Re. Application No. PCT/IB2019/054141. (9 Pages).
Notice of Allowability Dated Apr. 20, 2022 from US Patent and Trademark Office Re. U.S. Appl. No. 17/019,568. (4 pages).
Official Action Dated Sep. 29, 2023 from the US Patent and Trademark Office Re. U.S. Appl. No. 16/980,393. (43 pages).
Official Action Dated Sep. 22, 2021 from the US Patent and Trademark Office Re. U.S. Appl. No. 17/019,280. (26 pages).
Restriction Official Action Dated Jul. 13, 2021 from the US Patent and Trademark Office Re. U.S. Appl. No. 17/019,568. (5 pages).
Examination Report Dated Sep. 7, 2018 From the Government of India, Patent Office, Intellectual Property Building Re.: Application No. 309690.
Examination Report Dated Sep. 11, 2018 From the Government of India, Patent Office, Intellectual Property Building Re.: Application No. 309744.
International Preliminary Report on Patentability Dated Sep. 24, 2020 From the International Bureau of WIPO Re. Application No. PCT/IB2019/052016. (7 Pages).

(56) References Cited

OTHER PUBLICATIONS

International Preliminary Report on Patentability Dated Sep. 24, 2020 From the International Bureau of WIPO Re. Application No. PCT/IB2019/052008. (6 Pages).
International Preliminary Report on Patentability Dated Sep. 24, 2020 From the International Bureau of WIPO Re. Application No. PCT/IB2019/052010. (7 Pages).
International Preliminary Report on Patentability Dated Sep. 24, 2020 From the International Bureau of WIPO Re. Application No. PCT/IB2019/052014. (7 Pages).
International Preliminary Report on Patentability Dated Sep. 24, 2020 From the International Bureau of WIPO Re. Application No. PCT/IB2019/052017. (7 Pages).
International Search Report and the Written Opinion Dated Jul. 3, 2019 From the International Searching Authority Re. Application No. PCT/IB2019/052014. (16 Pages).
International Search Report and the Written Opinion Dated Jul. 3, 2019 From the International Searching Authority Re. Application No. PCT/IB2019/052017. (14 Pages).
International Search Report and the Written Opinion Dated Sep. 17, 2019 From the International Searching Authority Re. Application No. PCT/IB2019/054141. (11 Pages).
International Search Report and the Written Opinion Dated Jun. 26, 2019 From the International Searching Authority Re. Application No. PCT/IB2019/052016. (15 Pages).
International Search Report and the Written Opinion Dated Jun. 27, 2019 From the International Searching Authority Re. Application No. PCT/IB2019/052007. (12 Pages).
International Search Report and the Written Opinion Dated Jun. 27, 2019 From the International Searching Authority Re. Application No. PCT/IB2019/052008. (10 Pages).
International Search Report and the Written Opinion Dated Jun. 27, 2019 From the International Searching Authority Re. Application No. PCT/IB2019/052010. (17 Pages).
Notice of Amendment Dated Dec. 11, 2018 From the State Intellectual Property Office of the People's Republic of China Re. Application No. 201830508569.8. (2 pages).
Notification of Reason for Rejection Dated Jan. 30, 2019 From the Japanese Patent Office Re. Application No. 2018-019747. (2 Pages).
Official Action Dated Jun. 12, 2020 from the US Patent and Trademark Office Re. U.S. Appl. No. 29/640,027. (19 pages).
Official Action Dated Jun. 12, 2020 from the US Patent and Trademark Office Re. U.S. Appl. No. 29/640,032. (13 pages).
Official Action Dated Jun. 25, 2020 from the US Patent and Trademark Office Re. U.S. Appl. No. 29/653,164. (9 pages).
Cho "Characterization of Potential Probiotics Bacillus Subtilis CS90 From Soybean Paste (Doenjang) and Its Antimicrobial Activity Against Food-Borne Pathogens", Journal of Applied Biological Chemistry, 51(5): 285-291, 2008.
Gu et al. "The Preventive Effect and Therapeutic Effect of Spraying Agent of Bacillus Pab02 on Respiratory Infection in Broilers", Proceedings of the 10th in the 4th National Academic Seminar and Animal Micro-Ecology Enterprise Development Forum, p. 450-458, Aug. 1, 2010.
Jeon et al. "Screening and Characterization of Potential Bacillus Starter Cultures for Fermenting Low-Salt Soybean Past (Doenjang)", Journal of Microbiology and Biotechnology, 26(4): 666-674, Apr. 2016.
Ji et al. "Probiotic Bacillus Amyloliquefaciens SC06 Prevents Bacterial Translocation in Weaned Mice", Indian Journal of Microbiology, 53(3): 323-328, Published Online Mar. 16, 2013.
Wong et al. "An Antifungal Protein From Bacillus Amyloliquefaciens", Journal of Applied Microbiology, 105(6): 1888-1898, Dec. 2008.
Xie et al. "Isolation and Characterization of A Bacteriocin Produced by an Isolated Bacillus Subtilis LFB112 That Exhibits Antimicrobial Activity Against Domestic Animal Pathogens", African Journal of Biotechnology, 8(20): 5611-5619, Oct. 19, 2009.
Notice of Allowance Dated Mar. 9, 2022 together with Interview Summary Dated Feb. 16, 2022 from US Patent and Trademark Office Re. U.S. Appl. No. 16/645,509. (6 pages).
Notice of Allowance Dated Feb. 16, 2022 From the US Patent and Trademark Office Re. U.S. Appl. No. 17/019,281. (7 Pages).
International Preliminary Report on Patentability Dated Sep. 24, 2020 From the International Bureau of WIPO Re. Application No. PCT/IB2019/052007. (6 Pages).
Restriction Official Action Dated Jul. 7, 2021 from the US Patent and Trademark Office Re. U.S. Appl. No. 17/019,280. (5 pages).
Restriction Official Action Dated Jul. 7, 2021 from the US Patent and Trademark Office Re. U.S. Appl. No. 17/019,281. (5 pages).
Notice of Allowance Dated Oct. 26, 2022 from US Patent and Trademark Office Re. U.S. Appl. No. 17/019,596. (9 pages).
Notice of Allowance Dated Feb. 14, 2024 together with Interview Summary Dated Jan. 31, 2024 from the US Patent and Trademark Office Re. U.S. Appl. No. 17/057,727. (15 pages).
Notice of Allowance Dated Apr. 24, 2024 from US Patent and Trademark Office Re. U.S. Appl. No. 16/980,393. (9 pages).

* cited by examiner

Section A-A

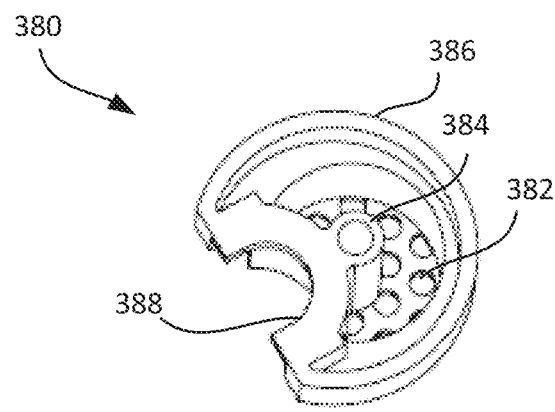
FIG. 9
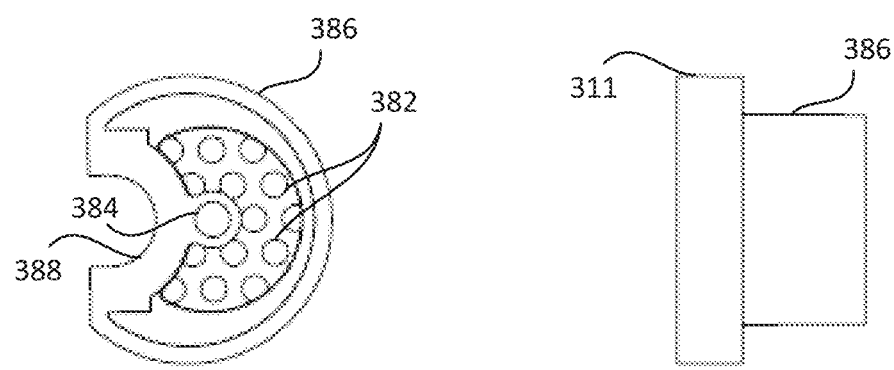
FIG. 10A
FIG. 10B
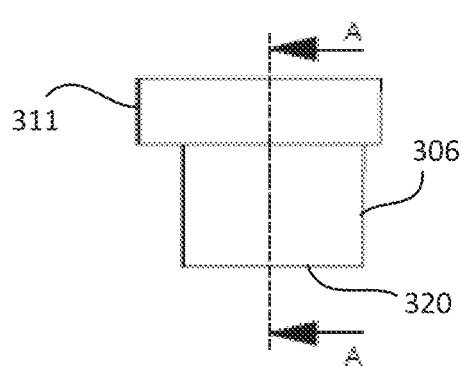
FIG. 10C
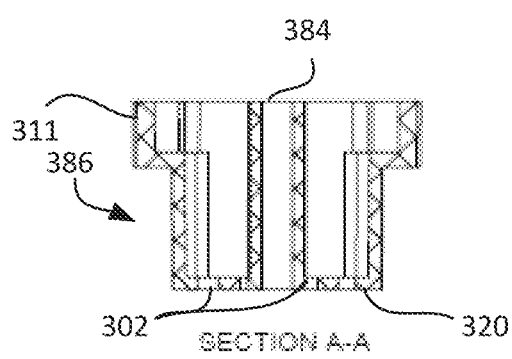
FIG. 10D

CARTRIDGE FOR AN AUTOMATED AEROSOL DISPENSING DEVICE

RELATED APPLICATIONS

This application is a National Phase of PCT Patent Application No. PCT/IB2019/052008 having International filing date of Mar. 12, 2019, which claims the benefit of priority under 35 USC § 119 (e) of U.S. Provisional Patent Application No. 62/641,441 filed on Mar. 12, 2018 The contents of the above applications are all incorporated by reference as if fully set forth herein in their entirety.

PCT Patent Application No. PCT/IB2019/052008 is also related to U.S. Provisional Patent Application Nos. 62/641,442, 62/641,443, 62/641,444, 62/641,445 and 62/641,464. The contents of the above applications are all incorporated by reference as if fully set forth herein in their entirety.

PCT Patent Application No. PCT/IB2019/052008 is also related to co-filed PCT Patent Applications Nos. PCT/IB2019/052007, PCT/IB2019/052010, PCT/IB2019/052017, PCT/IB2019/052014 and PCT/IB2019/052016 entitled "ELECTRONIC SAFETY FEATURE FOR AN AUTOMATED AEROSOL DISPENSING DEVICE"; "COMPOSITIONS COMPRISING BACTERIAL STRAINS AND USE THEREOF IN CONTROLLING PATHOGENIC MICROORGANISMS"; "COMPOSITIONS COMPRISING BACTERIAL STRAINS AND USE THEREOF IN CONTROLLING PATHOGENIC MICROORGANISMS"; "COMPOSITIONS COMPRISING BACTERIAL STRAINS AND USE THEREOF IN CONTROLLING PATHOGENIC MICROORGANISMS" and "COMPOSITIONS COMPRISING BACTERIAL STRAINS AND USE THEREOF IN CONTROLLING PATHOGENIC MICROORGANISMS", the contents of which are all incorporated by reference as if fully set forth herein in their entirety.

FIELD AND BACKGROUND OF THE INVENTION

The present invention, in some embodiments thereof, relates to a cartridge for an automated aerosol dispensing device and, more particularly, but not exclusively, to a cartridge configured for holding biological material to be dispensed with an automated aerosol dispensing device.

There are numerous devices known to atomize a liquid and deliver the atomized liquid into the surrounding air. Many of these devices are used to scent, purify, or humidify air in an enclosed room. Others of these devices are used to disinfect and deodorize. The atomized liquid may improve conditions in an indoor environment.

U.S. Pat. No. 8,986,610 entitled "Apparatus and method for dispersing liquid in aerosol," the contents of which is incorporated by reference herein, describes a system and method to deliver an atomized solution to the interior volume of a building or room utilizing a Venturi effect for the atomization. It is described that the solution may contain at least one active material including at least one of a medicament, probiotic, nutraceutical, or combinations thereof. The system includes a solution chamber; a Venturi configuration operatively associated with said solution chamber; an air inlet associated with a compressed air inlet source; an actuator and a sensor. The solution chamber may be in the form of a replaceable cartridge.

SUMMARY OF THE INVENTION

According to some example embodiments, a cartridge configured to contain a liquid to be dispensed by an automated aerosol dispensing device is pre-installed with a nebulizer (or atomizer) and a connector. According to some example embodiments, the connector is configured to operatively connect the nebulizer to a compressed air inlet source and actuator in the aerosol dispensing device and to direct the aerosol created toward a dedicated outlet in the aerosol dispensing device. In some example embodiments, the operative connection is made without requiring any physical contact between elements of the aerosol dispensing device and liquid included in the cartridge. In some example embodiments, the cartridge is configured to contain a liquid solution including live organisms, e.g. probiotics or other material that may be susceptible to contamination.

According to some example embodiments, a cartridge for an aerosol dispensing device includes an anti-spill cover to prevent spilling of a liquid contained in the cartridge during operative engagement of the cartridge with the aerosol dispensing device. For example, the anti-spill cover may prevent leakage of the liquid contained in the cartridge when the device is accidently tipped over. According to some example embodiments, during operative engagement of the cartridge with the aerosol dispensing device, liquid in the cartridge is extracted through the anti-spill cover. In some example embodiments, the liquid is atomized within the cartridge and the anti-spill cover is configured to allow the atomized liquid to pass through.

According to some example embodiments, at least one of a cartridge for an aerosol dispensing device and the aerosol dispensing device includes a mechanism for stirring liquid contents of the cartridge. Optionally, liquid content in the cartridge may be stirred continuously or periodically during use to maintain a substantially constant concentration of active material over a volume of the liquid.

According to an aspect of some example embodiments, there is provided a connector configured to support a nebulizer inside a cartridge, the connector comprising: an annular wall; a conduit; and a plurality of spokes between the annular wall and the conduit; wherein the plurality of spokes define openings therebetween and wherein the annular wall is shaped and sized to be fitted into a collar of a bottle.

Optionally, the conduit is aligned with a central axis of the annular wall and the spokes surround the conduit.

Optionally, the conduit includes a first end configured to connect to a nebulizer and a second end opposite the first end configured to connect to an air outlet nozzle and wherein the first end includes screw threads.

Optionally, the screw threads are formed in an inner surface of the annular wall.

Optionally, the second end is configured to provide a friction fit connection with the air outlet nozzle.

Optionally, the second end is configured to have a diameter that is smaller than a diameter of the air outlet nozzle and to plastically deform based on connection with the air outlet nozzle.

According to an aspect of some example embodiments, there is provided a cartridge comprising: a housing configured to house a liquid; a collar defining an opening into the cartridge; the connector according to the present invention; and a nebulizer held within the housing with the connector.

Optionally, the cartridge is configured to be disposable.

Optionally, the cartridge further comprises a gasket positioned on the connector, wherein the gasket is configured to provide a sealed connection with a device configured to actuate atomization of the liquid.

Optionally, the cartridge further comprises the liquid, wherein the liquid is water based and wherein the nebulizer is configured to atomize the liquid.

Optionally, the nebulizer is positioned to form an aerosol within a volume of the housing.

Optionally, the cartridge includes a mechanical stirring element configured to stir the liquid within the housing based on actuation with an external actuator.

According to an aspect of some example embodiments, there is provided a cartridge comprising: a housing configured to house a liquid; and an adaptor fixed to the housing and configured to fluidly connect the liquid in the housing to an actuator for actuating atomization of the liquid, wherein the adaptor includes a nebulizer that extends within the housing and is configured to form an aerosol within the housing.

Optionally, the adaptor is a single part formed from a polymer material.

Optionally, the adaptor includes an inlet configured to receive a nozzle providing compressed air to the nebulizer and an opening through which the aerosol is expelled.

Optionally, the housing includes collar defining an opening to the housing and wherein the adaptor includes an annular portion that is fitted in the collar.

Optionally, the nebulizer is integrated in the annular portion.

Optionally, the adaptor extends outside the housing, wherein a portion of the adaptor that extends outside the housing includes an alignment element configured to align with a matching element on a device configured to actuate the atomization.

Optionally, the adaptor includes an inlet configured to receive a nozzle providing compressed air to the nebulizer wherein the alignment element is configured to align the inlet with the nozzle.

Optionally, the cartridge is configured to be disposable.

Optionally, the cartridge further comprises a straw configured to connect to the adaptor.

Optionally, the cartridge includes a mechanical stirring element configured to stir the liquid within the housing based on actuation with an external actuator.

According to an aspect of some example embodiments, there is provided an anti-spill cover configured to be fitted in an outlet of a cartridge comprising: a surface formed with a plurality of holes, wherein the holes are sized to deter leakage of a water-based solution housed within the cartridge and is tipped over; and a wall surrounding the surface, wherein the wall is sized and shaped to fit into the outlet of the cartridge.

Optionally, the holes have a diameter of between 1.5-2 mm.

Optionally, the cover includes 7-15 holes on the surface.

Optionally, the walls are also formed with holes.

Optionally, the cover includes a hollow column configured to collect condensation formed over the cover.

Optionally, the wall includes a concave portion configured to fit around an air inlet channel.

Optionally, the surface and wall is an integral part formed from a polymer material.

According to an aspect of some example embodiments, there is provided an adaptor configured to be fitted in an outlet of a cartridge and to fluidly connect the cartridge to an aerosol dispensing device, the adaptor comprising: an annular portion configured to fit on the outlet of the cartridge; a nebulizer that extends from the annular portion into the cartridge and is configured to form an aerosol within the cartridge; and the anti-spill cover, wherein the anti-spill cover is configured to cover the outlet while providing a passage of the atomized liquid.

Optionally, the annular portion and the nebulizer is an integral part.

Optionally, the annular portion, the nebulizer and the anti-spill cover is an integral part.

Optionally, the nebulizer includes a Venturi configuration.

According to an aspect of some example embodiments, there is provided a cartridge comprising: a housing configured to house a liquid; an adaptor fixed to the housing and configured to fluidly connect the housing to an actuator for actuating atomization of the liquid, wherein the adaptor includes a nebulizer that extends within the housing and is configured to form an aerosol within the housing; and the anti-spill cover configured to cover an outlet through which the adaptor is fluidly connects the housing to the actuator.

Optionally, the adaptor includes an inlet configured to receive a nozzle providing compressed air to the nebulizer and an opening through which the aerosol is expelled.

Optionally, the housing includes collar defining an opening to the housing and wherein the adaptor includes an annular portion that is fitted in the collar.

Optionally, the nebulizer extends from the annular portion.

Optionally, the cartridge is configured to be disposable.

According to an aspect of some example embodiments, there is provided a cartridge comprising: a housing configured to house a liquid; a nebulizer held within the housing; a connector configured to support the nebulizer inside the housing; and a mechanical or magnetic stirring element configured to stir the liquid within the housing based on actuation with an external actuator.

Optionally, the mechanical stirring element is a stir bar and wherein the stir bar is configured to based applying a rotating magnetic field.

Optionally, the mechanical stirring element is a mechanical stirrer including an elongated rod, wherein a distal end of the elongated rod extends outside of the housing and is configured to engage a motor external to the cartridge.

According to an aspect of some example embodiments, there is provided an aerosol dispensing device comprising: an atomizer configured to atomize a liquid contained in a cartridge; a first actuator configured to actuate activity of the atomizer; a second actuator configured to actuate stirring the liquid contained in the cartridge; and a controller control operation of the first actuator and the second actuator.

Optionally, the second actuator is a motor configured to engage a mechanical stirrer extending into the cartridge.

Optionally, the second actuator is configured to rotate a magnetic field and to spin a stir bar within the cartridge based on the actuated magnetic field that is rotated.

Optionally, the second actuator is at least on speaker configured to emit sound waves.

Optionally, the controller is configured to active the second actuator in coordination with dispensing the aerosol.

Optionally, the device includes a sensor configured to sense a gradient in concentration of the liquid across a volume of the liquid, wherein the controller is configured to active the second actuator based on output from the sensor.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 9 is a perspective view of an example anti-spill cover in accordance with some example embodiments;

FIGS. 10A, 10B, 10C and 10D are top, side and cross-sectional views of an example anti-spill cover in accordance with some example embodiments;

DESCRIPTION OF SPECIFIC EMBODIMENTS OF THE INVENTION

Figure 1A:
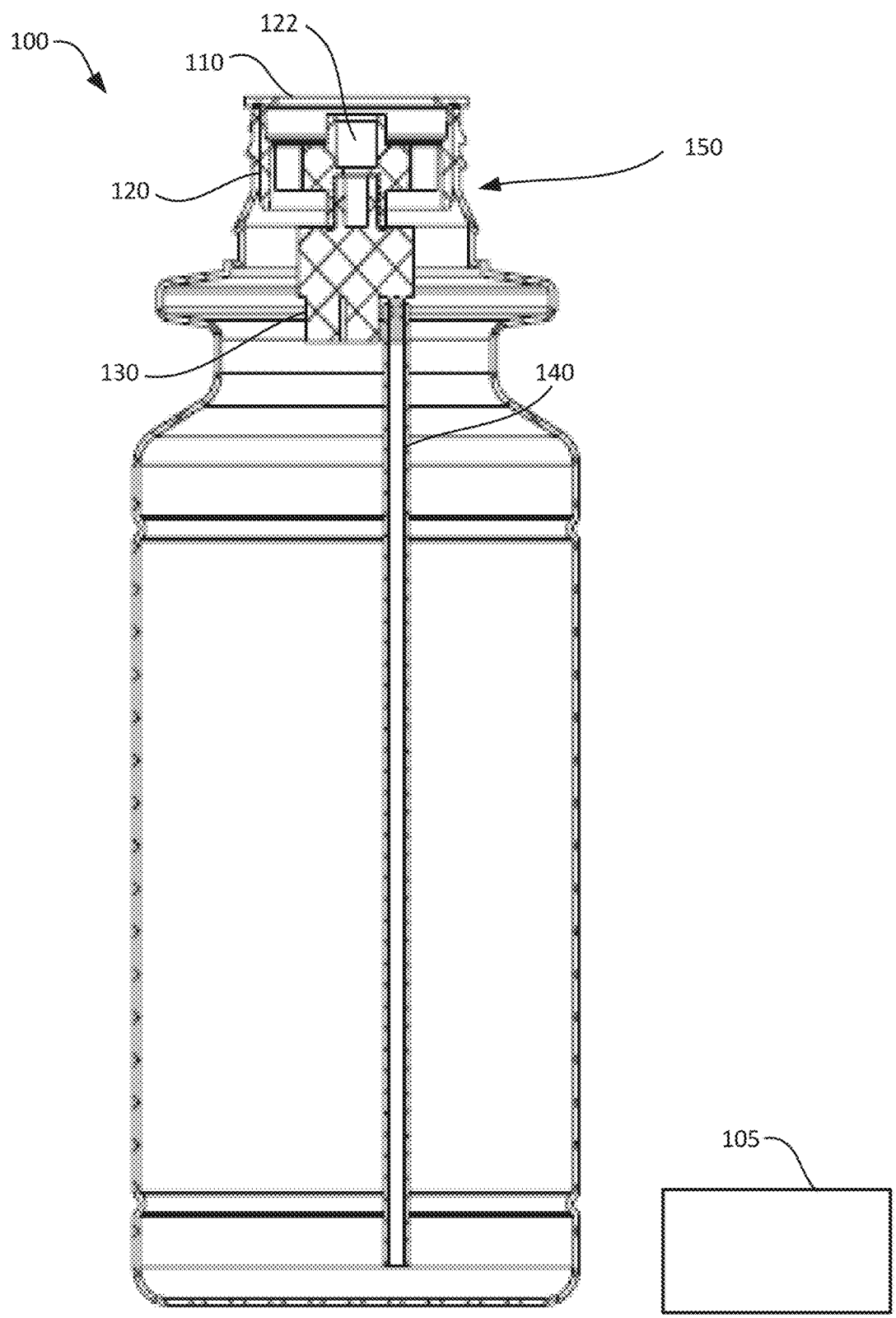
FIGS. 1A and 1B is simplified schematic cross-sectional view of an example bottle shaped cartridge including a nebulizer with connector fitted on a collar of the bottle and the example bottle installed in an aerosol dispensing device both in accordance with some example embodiments.

The present invention, in some embodiments thereof, relates to a cartridge for an automated aerosol dispensing device and, more particularly, but not exclusively, to a cartridge configured for holding biological material to be dispensed with an automated aerosol dispensing device.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

According to some example embodiments, a cartridge includes a housing configured to hold a liquid that is to be atomized, a nebulizer configured to atomize the liquid and optionally a connector configured to hold the nebulization nozzle head in the cartridge. The housing together with the nebulizer and the connector integrated therein is configured to be replaced once the liquid stored therein is used up. The nebulizer may include a Venturi tube configured to impose a Venturi effect, an air inlet into the Venturi tube and an outlet via which the atomized liquid may be expelled. Optionally, a straw is connected to the nebulizer and is configured to suction flow from within the cartridge toward the Venturi tube. According to some example embodiments, the nebulizer is held in place and operatively connected to the aerosol dispensing device with the dedicated connector. In some example embodiments, the dedicated connector is configured to align the nebulizer with an outlet of a compressed air source and to direct the aerosol formed toward an outlet defined by the aerosol dispensing device.

According to some example embodiments, the cartridge integrated with the nebulizer may provide better protection against contamination when operating the dispensing device with the cartridge. Contamination may be a major concern when dealing with biological material. In known aerosol dispensing devices, a reusable nebulizer attached to the device is immersed in the liquid to be atomized during installation. The reusable nebulizer may accumulate bacteria over time and immersion of the nebulizer in the liquid may lead to contamination.

The present inventors have found that forming the cartridge with a disposable, e.g. single use nebulizer may be advantageous. One advantage may be that the cartridge with the integrated nebulizer provides for installing the cartridge and operating aerosol dispensing device without immersing any structure of the aerosol dispensing device into the contents of the cartridge. By avoiding immersion of a structure configured for reuse, the risk of contamination may be reduced. Another advantage may be that authenticity of the cartridges may be further assured by requiring the cartridges to include the nebulizer. Unauthorized replication of the cartridge may be difficult and expensive when the cartridge is required to include the nebulizer. Yet another advantage of forming the cartridge with a disposable, e.g. single use, nebulizer may be to avoid potential dust or particle build up in the Venturi tube over time that may lead to blockage. In some example embodiments, a diameter of the Venturi configuration may be small especially when it is configured for atomizing a water based solution and therefore it may be prone to blockage over an extended period of time. A single use nebulizer may be less prone to blockage.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

According to some example embodiments, it is desired to continuously or periodically stir contents of a bottle that is installed in the aerosol dispensing device to avoid gradients in the bacterial load along a height or across a volume of the bottle due to settling of the bacteria. By maintaining a substantially same concentration of bacteria, the dosage that is dispensed may be better controlled. In some example embodiments, one or more of the bottle and the aerosol dispensing device may include a mechanism for stirring contents within the bottle. In some example, the magnetic stirring may be applied based on including a stir bar in the bottle and spinning the stir bar with an external magnetic field. In another example, sound waves may be emitted within bottle to stir the contents of the bottle. In other examples, the bottle may include a mechanical stirrer that may be rotated with a motor installed in the aerosol dispensing device. Stirring may be actuated continuously, periodically or on demand. Optionally, a controller in aerosol dispensing device may control frequency and duration of the stirring. Optionally, aerosol dispensing device may include a sensor configured to sense settling of the bacteria and stirring may be based on output from the sensor.

Figure 1B:
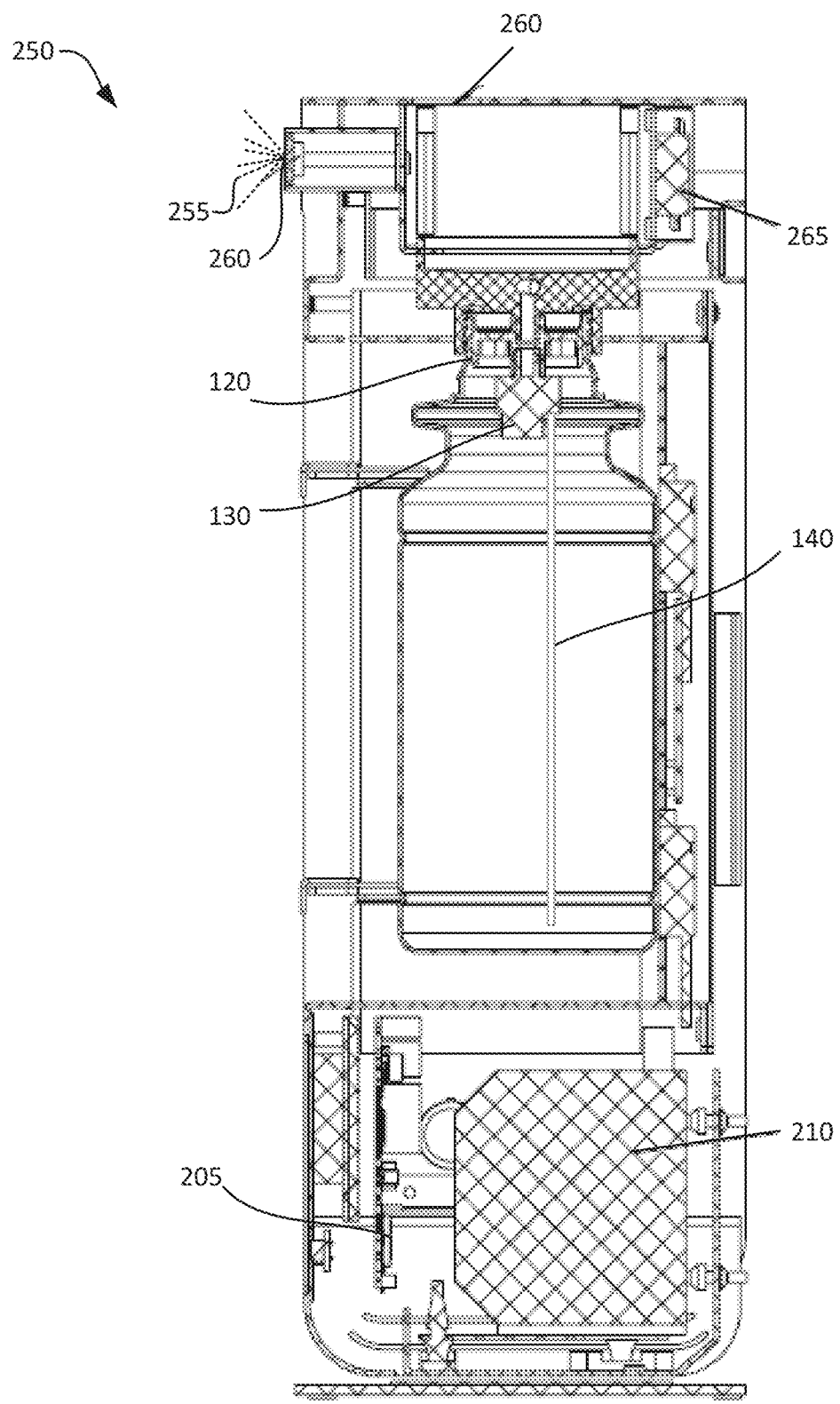
Figure 2A:
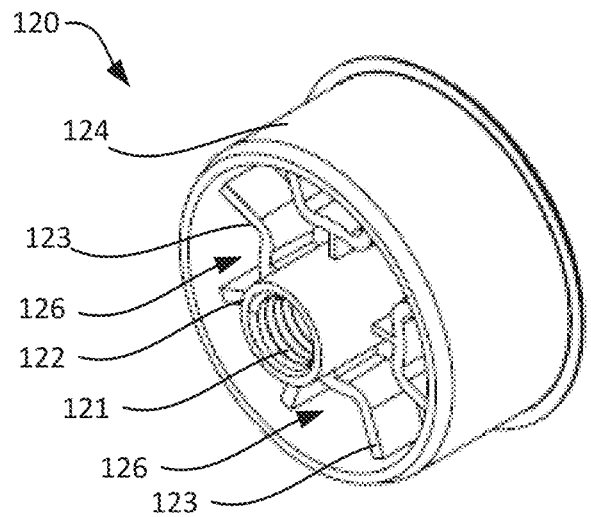
FIGS. 2A, 2B, 2C and 2D are perspective, top, side and cross sectional views of an example connector in accordance with some example embodiments.
Figure 2B:
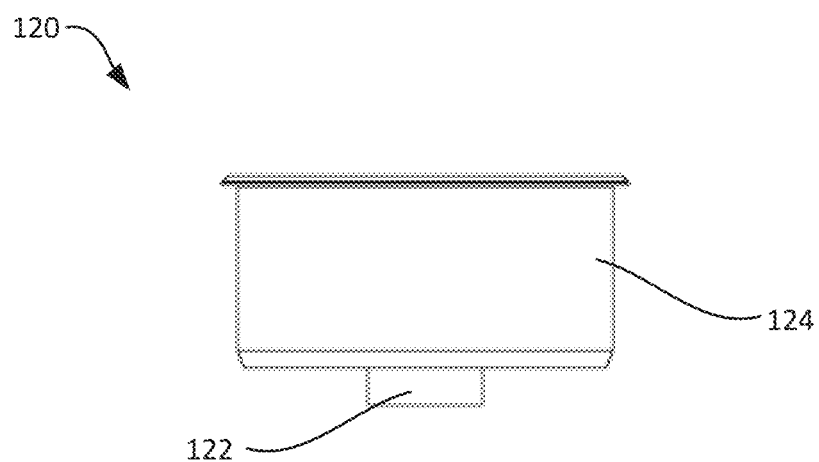
Figure 2C:
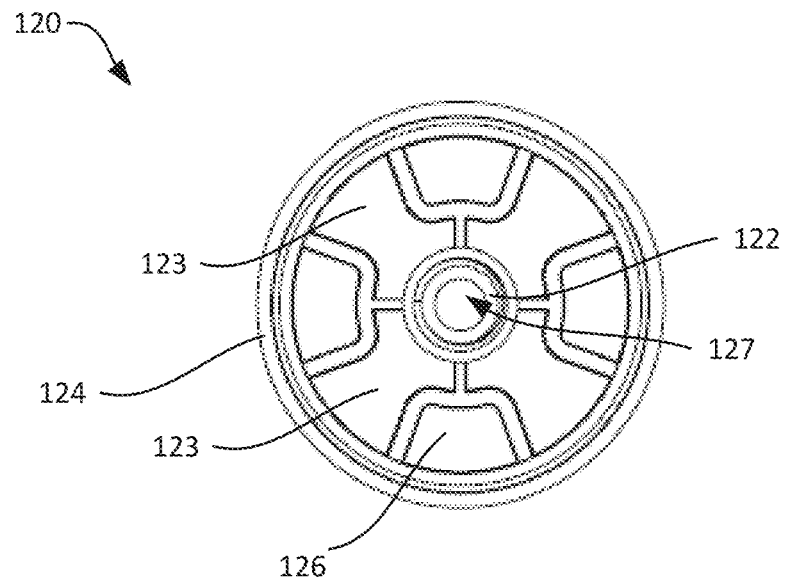
Figure 2D:
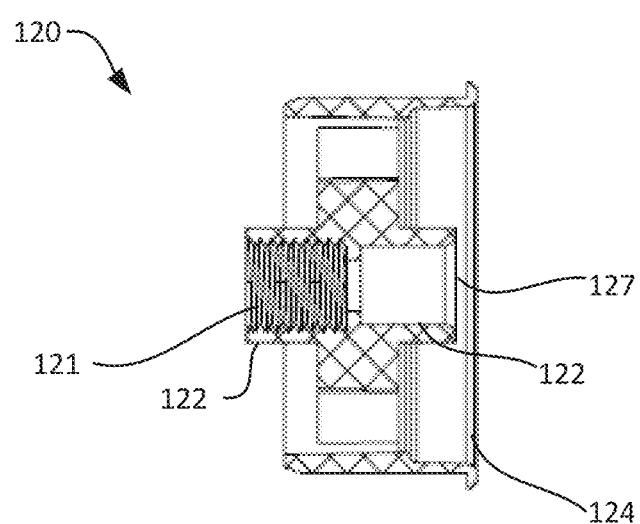

Reference is now made to FIG. 1A and FIG. 1B showing simplified schematic cross-sectional view of an example bottle shaped cartridge including a nebulizer fitted on a lip of the bottle and the example bottle installed in an aerosol dispensing device both in accordance with some example embodiments. A bottle 100 configured to hold a liquid to be atomized is installed with a nebulizer 130. Nebulizer 130 may be held in place with a connector 120. Connector 120 may be fitted, e.g. friction fitted into a lip or collar 150 of bottle 100. In some example embodiments, connector 120 includes a conduit 122 configured to connect with nebulizer 130 at one end and to connect to a compressed air source 210 of an aerosol dispensing device 250 at an opposite end. In some example embodiments, injection of air from a compressed air source actuates creation of an aerosol through nebulizer 130 within bottle 100. The aerosol 255 may then rise through openings defined in connector 120 toward one or more outlets 260 defined in aerosol dispensing device 250. Optionally, a fan 265 in aerosol dispensing device 250 suctions and disperses aerosol 255. Optionally, a controller 205 is configured to control operation of aerosol dispensing device 250.

Nebulizer 130 may optionally be an off the shelf nebulizer. In some example embodiments, connector 120 and nebulizer 130 may be integrated into a single part, e.g. a single part formed by injection molding specifically configured for fitting onto lip 150. Optionally, bottle 100 may additionally include a gasket 110 configured to provide a sealed connection with an aerosol dispending device. Typically, bottle 100 is filled with the liquid and sealed with a removable cap 105. Cap 105 is typically removed prior to installing bottle 100 into aerosol dispending device 250.

Typically, a straw 140 is positioned on nebulizer 130 and the straw is configured to directed suctioned fluid into nebulizer 130. Straw 140 may be sized to extend substantially toward a bottom of bottle 100. In some example embodiments, connector 120 and optionally nebulizer 130 is formed with a polymer such as polypropylene. Optionally straw 140 may be formed with a softer polymer, e.g. polyethylene.

In some example embodiments, the liquid to be atomized is water based and nebulizer 130 is selected or defined to be suitable for atomizing a water based solution. In some example embodiments, during production connector 120 with nebulizer 130 is fitted onto bottle 100 after bottle 100 is filled with the liquid to be atomized. In some example embodiments, bottle 100 includes a breakable seal between cap 105 and gasket 110 that is configured to be broken during or just prior to installation.

Reference is now made to FIGS. 2A, 2B, 2C and 2D are perspective, top, side and cross sectional views of an example connector in accordance with some example embodiments. In some example embodiments, connector 120 includes a central conduit 122 that is surrounded with a plurality of openings 126 separated by spokes 123. In other examples conduit may be off-centered. In some example embodiments, openings 126 are defined to be large enough to provide substantially unobstructed flow of the aerosol created in bottle 100. Spokes 123 may extend from a wall 124 and may be sized and shape to provide stability to wall 124 so that it may be held in place on the lip of the bottle. In some example embodiments, wall 124 is annular and shaped to fit into a lip of a bottle. Optionally, openings 126 cover 20-70% of the surface area of connector 120. In some example embodiments, conduit 122 may include screw threads 121 at one end configured to receiving the nebulizer.

Connector 120 may typically be formed from a polymer, e.g. polypropylene. Optionally, a diameter of conduit 122 on an opposite end from the end including the screw threads is sized to receive a nozzle or tube in the aerosol dispensing device through which compressed air is delivered. In some example embodiments, a diameter of conduit opening 127 is configured to be smaller than the size of the nozzle so that engagement with the nozzle or tube results in plastic deformation of the conduit 122. Optionally, sizing the diameter of opening 127 so that is smaller than the size of the nozzle or tube connected to it may improve the sealed connection between the parts and may also prevent reusing the bottle.

Figure 3:
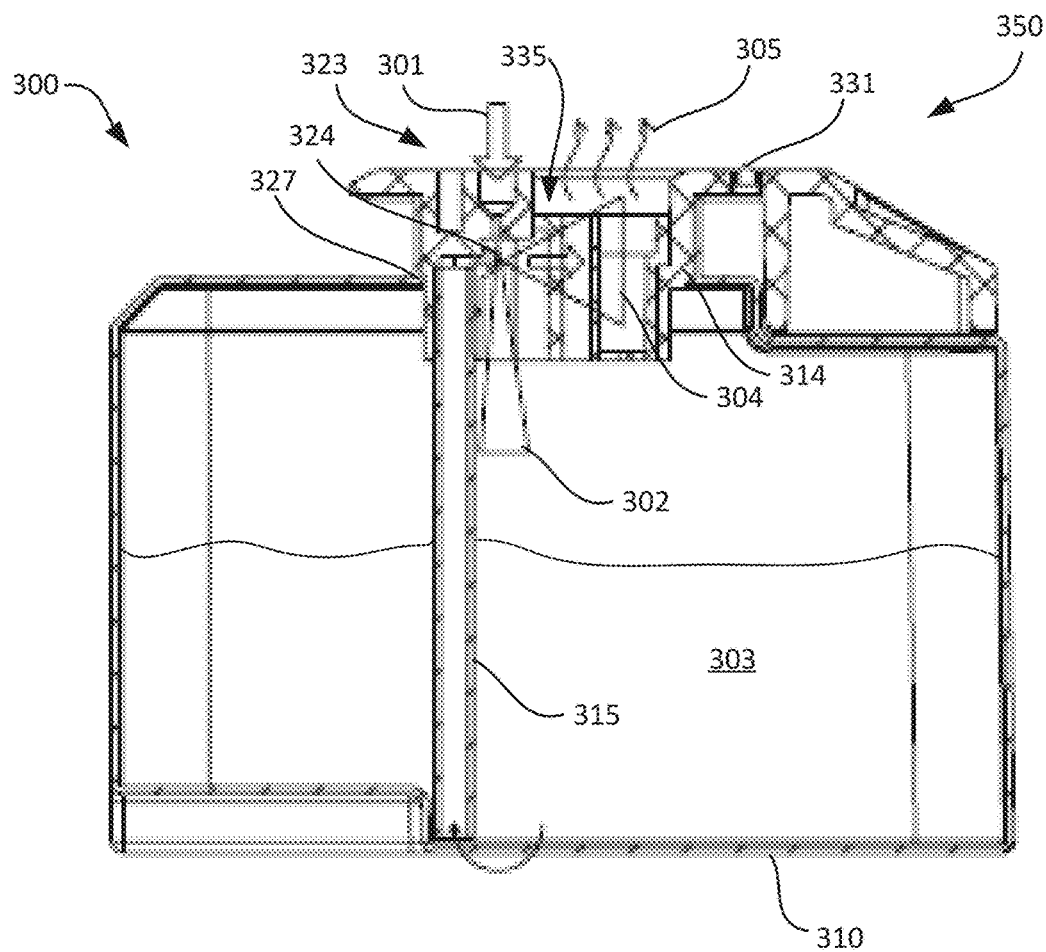
FIG. 3 is schematic cross-sectional view of another example cartridge including a nebulizer integrated therein in accordance with some example embodiments.

Reference is now made to FIG. 3 showing schematic cross-sectional view of another example cartridge including a nebulizer integrated therein in accordance with some example embodiments. In some example embodiments a cartridge 300 may include a housing 310 with an opening 335 defined by a surrounding collar 327 through which a liquid may be inserted and an aerosol may be expelled. Optionally, housing 310 may be in the form of a cuboid. In some example embodiments, cartridge 300 additionally includes an adaptor 350 that is fitted on collar 327. Optionally, adaptor 350 includes an annular portion 314 that is fitted into collar 327, e.g. friction fitted. Adaptor 350 may be configured to operatively connect cartridge 300 to an aerosol dispensing device that is configured to actuate atomization of a liquid stored in housing 310. According to some example embodiments, adaptor 350 includes a nebulizer 323 with Venturi tube configured to impose a Venturi effect. Nebulizer 323 may include an air inlet 301 configured for receiving compressed air, an air outlet 302 through which the air may be expelled in housing 310 and suction inlet 324 through which liquid 303 enters the Venturi tube, and an aerosol output 304 through which the aerosol is released. Liquid 303 may be sucked into nebulizer 323 with straw 315.

In some example embodiments, adaptor 350 additionally includes an aligning element 331 that is configured to secure cartridge 300 in place when inserted into the aerosol dispensing device. When secured, a nozzle delivering compressed air may be aligned with air inlet 301.

Figure 4:
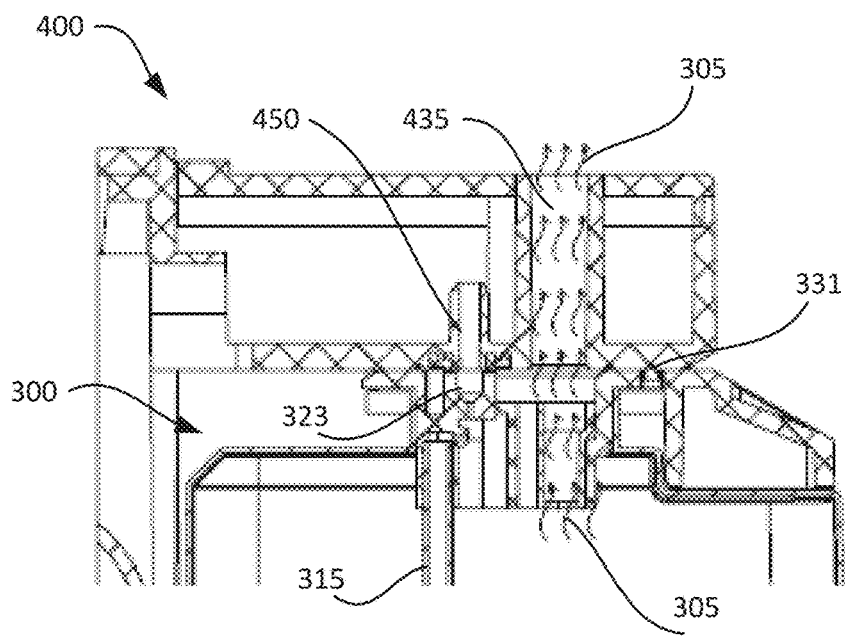
FIG. 4 is a cross-sectional view showing connection between a nebulizer integrated in a cartridge and a portion of an aerosol dispensing device in accordance with some example embodiments.
Figure 5:
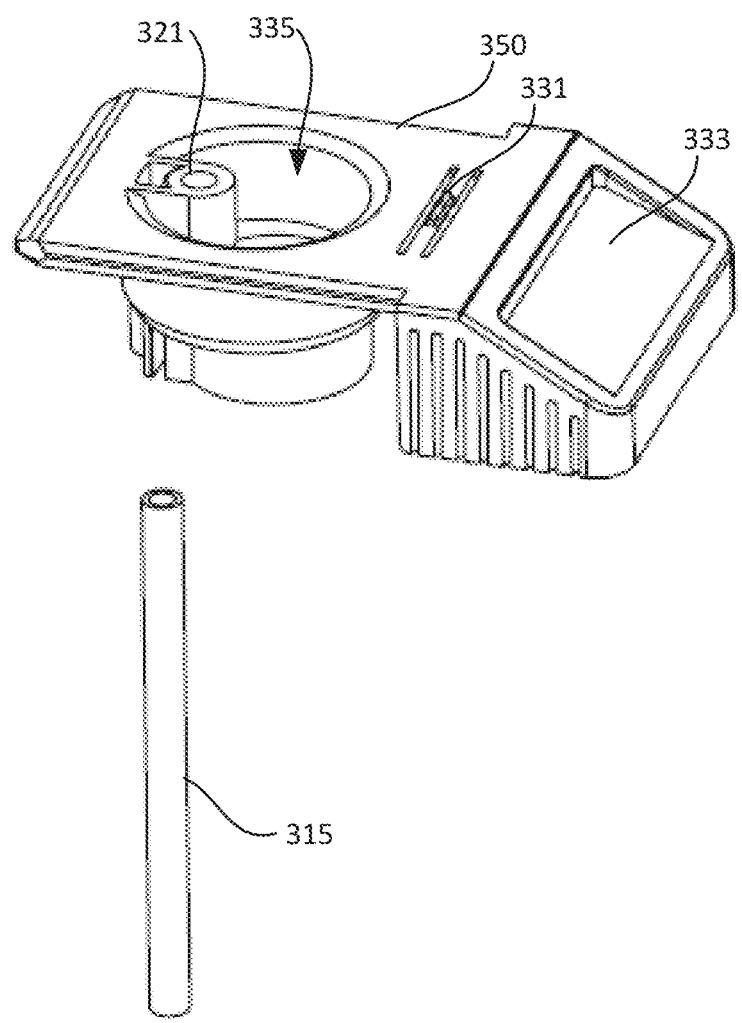
FIG. 5 is an exploded view of an example nebulizer configured to be installed on a cartridge in accordance with some example embodiments.
Figure 6A:
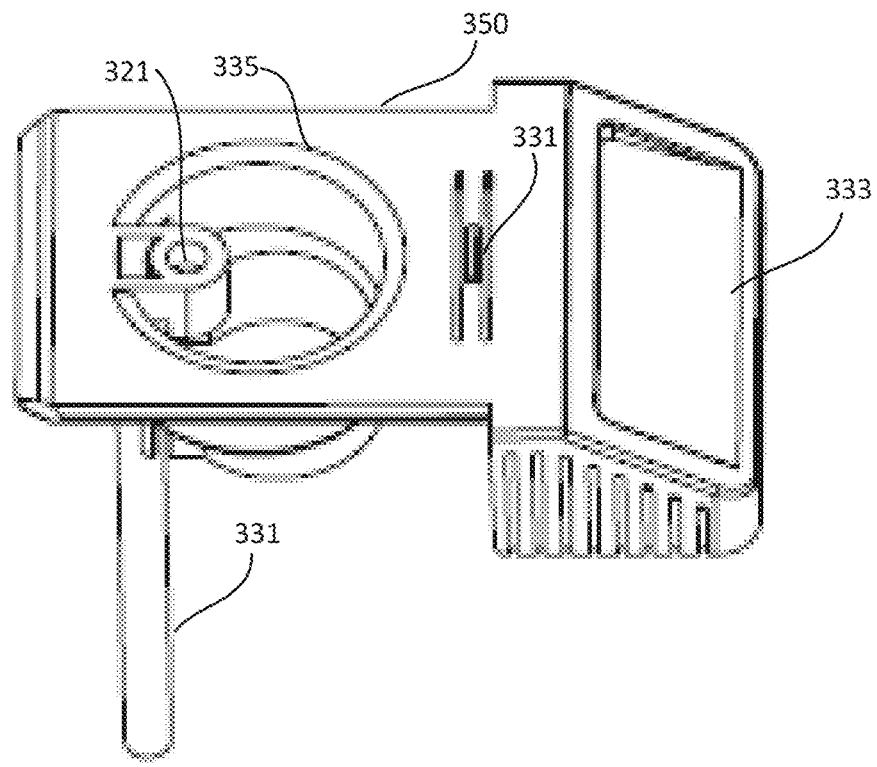
FIGS. 6A, 6B, 6C and 6D is an example perspective, side view, top and cross-sectional view of an example nebulizer in accordance with some example embodiments.
Figure 6B:
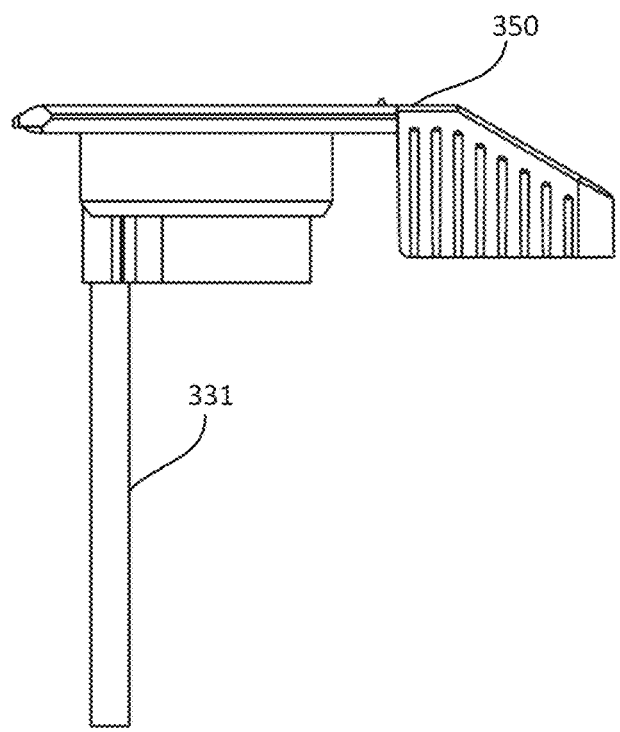
Figure 6C:
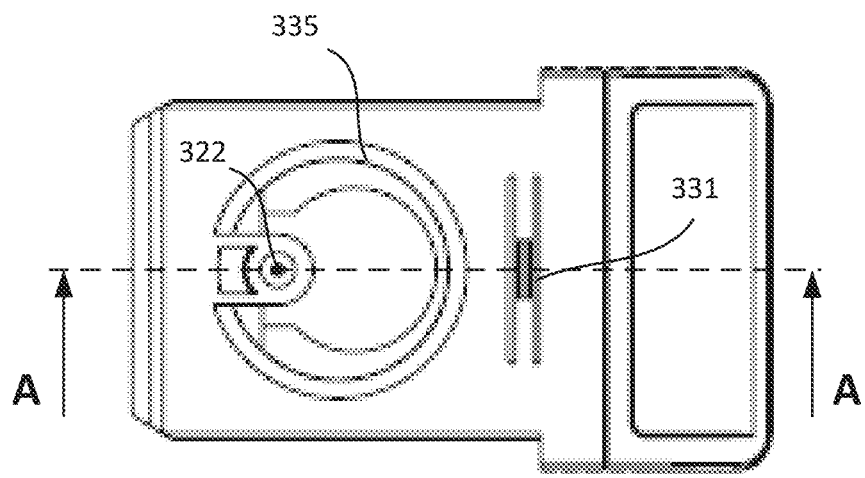
Figure 6D:
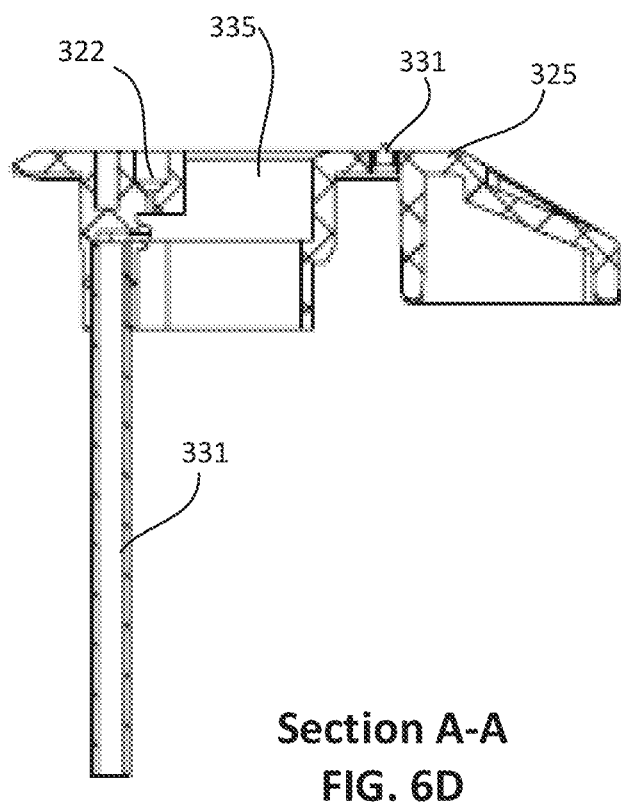
Figure 7:
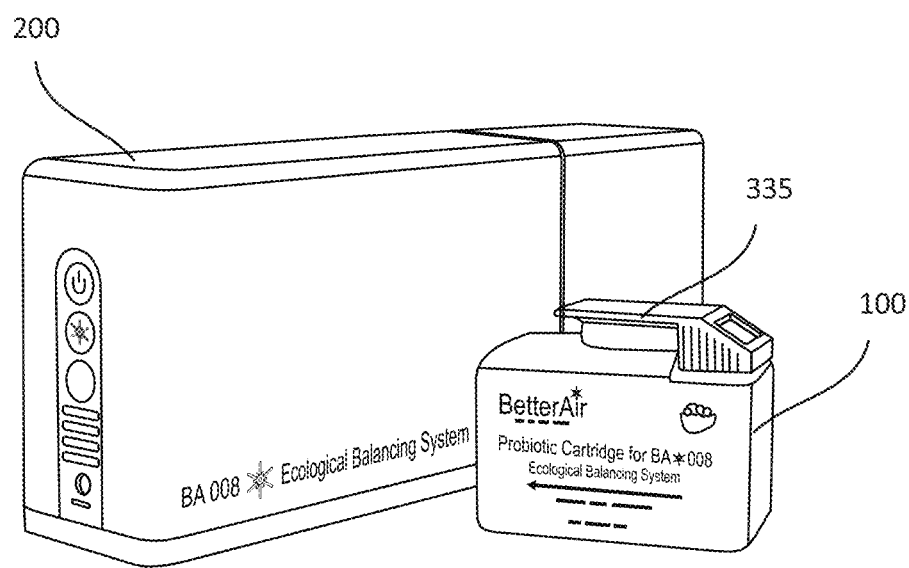
FIG. 7 is an example prior art aerosol dispensing device with an example replaceable cartridge.
Figure 8A:
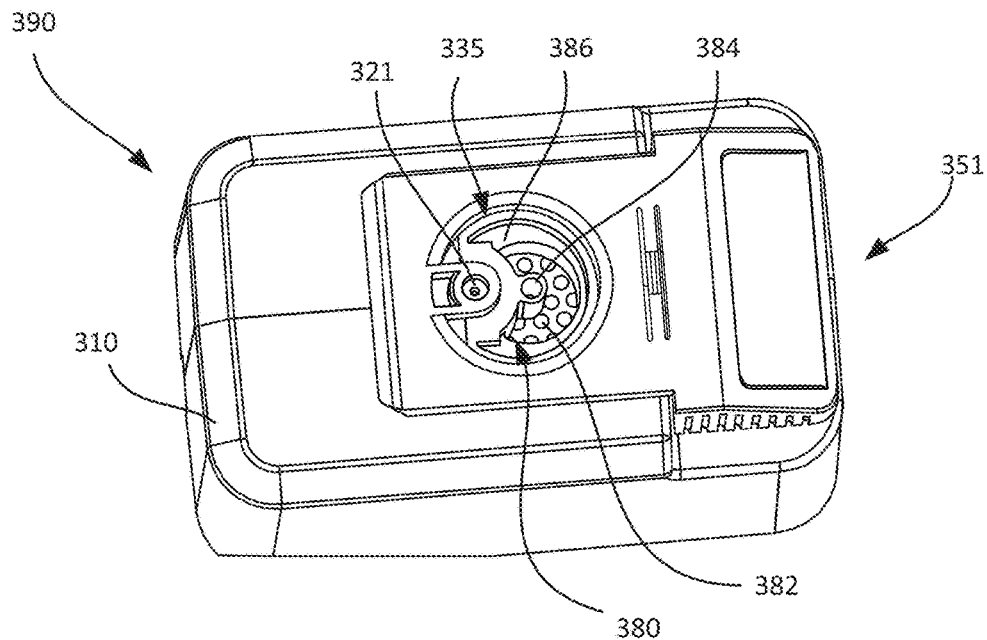
FIGS. 8A and 8B are perspective and schematic cross sectional views of an example cartridge in accordance with some example embodiments.
Figure 8B:
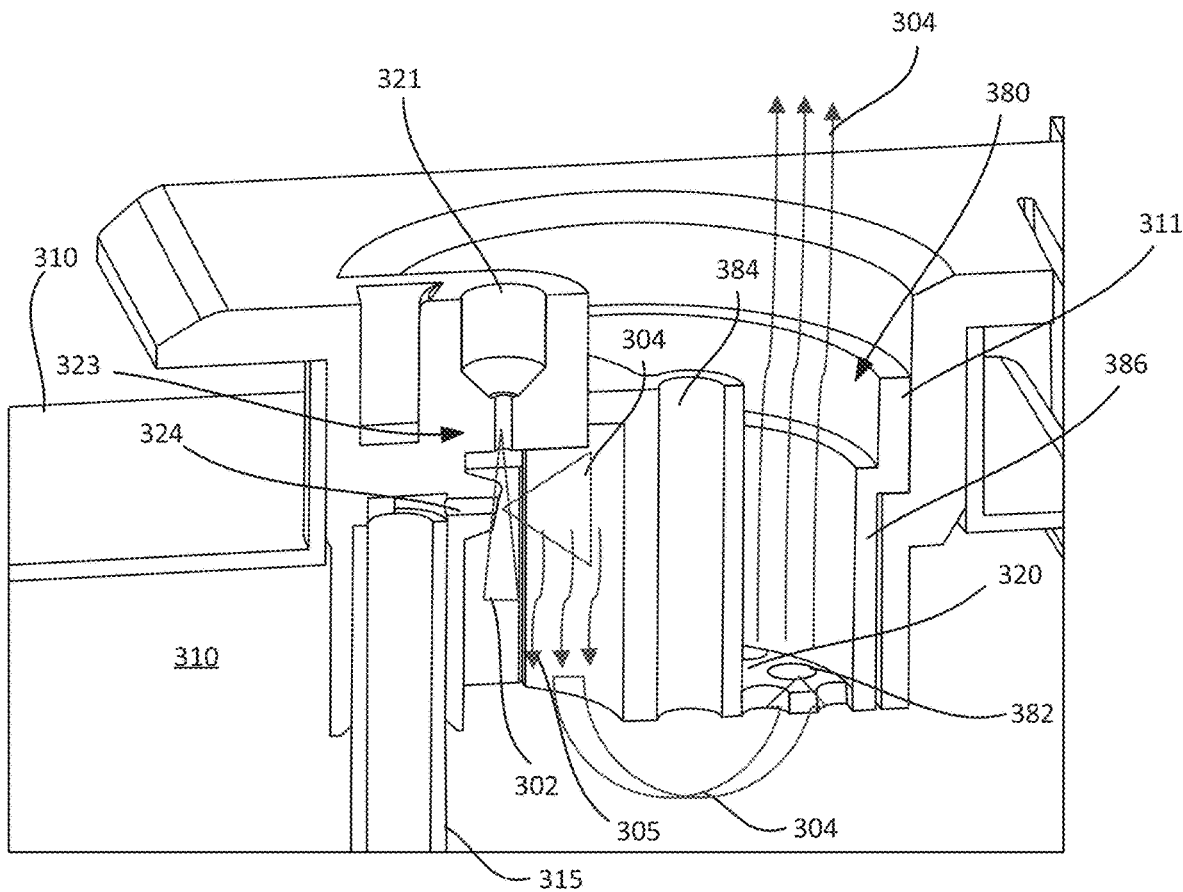

Reference is now made to FIG. 4 showing a cross-sectional view showing connection between a nebulizer integrated in a cartridge and a portion of an aerosol dispensing device in accordance with some example embodiments. In some example embodiments, cartridge 300 is fitted onto a head of an aerosol dispensing device 400. In some example embodiments, an aligning element 331 snaps into place when cartridge 300 is properly fitted into device 400. While properly fitted, inlet into Venturi configuration 323 is aligned with a nozzle 450 through which compressed air may be introduced and opening 335 may be aligned with outlet 435. Alternatively, opening 335 may be configured to indirectly align with outlet 450 so that a velocity of flow of aerosol 305 may be reduced as it is being expelled from outlet 450.

Reference is now made to FIG. 5 showing an exploded view of an example nebulizer configured to be installed on a cartridge and to FIGS. 6A, 6B, 6C and 6D showing an example perspective, side view, top and cross-sectional view of an example nebulizer, all in accordance with some example embodiments. According to some example embodiments, adaptor 350 may include a nebulizer with an inlet 321 for receiving a nozzle through which compressed air may be introduced and an opening 335 through which the aerosol formed may be expelled. Inlet 321 is part of nebulizer that is also integrated as part of adaptor 350. A straw 331 may be formed as a separate component that may be connected to adaptor 350. In some example embodiments, adaptor 350 is formed from a rigid polymer, e.g. polypropylene. Optionally, adaptor 350 additionally includes one or more aligning or locking elements 331 that may help align cartridge 300 with mechanical elements of an aerosol dispensing device. Adaptor 350 may additionally include a tab 333 that a user is configured to push to insert the cartridge into the device.

Reference is now made to FIG. 7 showing an example aerosol dispensing device with an example replaceable cartridge. Aerosol dispensing device 200 is an example device that is configured to be installed with replaceable cartridges. Device 200 may be for example an Ecological Balancing System BA008 manufactured by BetterAir International Ltd. in Hong Kong. The cartridges, such as example cartridge 100 may include a liquid to be dispersed. The liquid may be extracted from cartridge 100 through an outlet 335. Outlet 335 may be annular, e.g. shaped as a collar or neck of a bottle. When cartridge 100 is inserted into device 200 and device 200 is operated, a nebulizer of device 200 may a surrounding environment.

Device 200 may be a free standing device that may be placed on a shelf or other surface of an indoor environment. When device 200 is free standing it may be prone to being accidently tipped over and as a result contents of cartridge 100 may spill out. For example, device 200 may accidently tip over when being moved around by a user or when another object in the vicinity is moved and accidently engages device 200. Spilling of the liquid may be wasteful and may at times completely empty contents of cartridge 100.

According to some example embodiments, an anti-spill cover may be integrated on a collar of a cartridge containing a liquid to be atomized with an aerosol dispensing device, e.g. device 200. In some example embodiments, the anti-spill cover includes a surface formed with a plurality of holes, e.g. perforated surface through which the atomized liquid may exit the cartridge, e.g. cartridge 100. In some example embodiments, the holes are configured to be large enough to provide substantially unobstructed passage of the atomized liquid and small enough to create a surface tension that may block leakage of the liquid (the non-atomized liquid) when the cartridge is tipped over. Optionally, a diameter of the holes is between 1-2.5 mm, e.g. 1.5-2 mm or 1.7 mm. Optionally, the surface may be formed with 5-20 holes, e.g. 7-15 holes. Optionally, the holes are configured to create a surface tension that blocks flow of a water based liquid.

According to some example embodiments, the anti-spill cover may include the perforated surface and a surrounding wall that is configured to fit into an outlet of a cartridge. Optionally, the cover may be fitted with a friction fit. In some example embodiments, the anti-spill cover is integrated with a connector configured to connect to a nebulizer or is integrated with the nebulizer. Optionally, the outlet is integrated with a nebulizer and the anti-spill cover is fitted alongside the nebulizer. In some example embodiments, the anti-spill cover may be shaped to leave room for receiving a nebulizer in the outlet or for receiving a connector to a nebulizer during installation of the cartridge in the aerosol dispensing device. As used herein the term nebulizer is not limited to a Venturi type nebulizer and may include other types of atomizers that atomize a liquid, e.g. ultrasound nebulizer and mesh nebulizer. As used herein the term atomizer is used interchangeably with the term nebulizer and has the same meaning as the term nebulizer.

In some example embodiments, the anti-spill cover additionally includes a channel configured to collect condensation fluid from above the perforated surface, e.g. toward the outside the cartridge and direct the condensation fluid back into the cartridge. Optionally, the channel may provide venting out air trapped inside the bottle in exchange for fluid entering in much like a chimney.

Reference is now made to FIGS. 8A and 8B showing perspective and schematic cross sectional views of an example cartridge in accordance with some example embodiments. A cartridge 390 may include a housing 310 configured to store a liquid and an adaptor 351 that is fitted onto an outlet 335 from which the liquid may be extracted by an aerosol dispensing device. In some example embodiments, an anti-spill cover 380 is fitted into outlet 335 and is configured to prevent leakage of liquid stored in housing 310 when the cartridge 390 accidently tips over. A diameter of outlet 335 may be 1-5 cm, e.g. 1.5-3.5 cm. Anti-spill cover 380 may include a surface with holes 382 that covers outlet 335 and a surrounding wall 386 that is sized to fixedly held in outlet 335. In some example embodiments, surrounding wall 386 includes a rim 311 with extended diameter and may provide additional structural support for cover 380. A diameter of holes 382 may be between 1-2.5 mm, e.g. 1.5-2 mm or 1.7 mm. Distance between the holes may be between 0.2-2 mm. Optionally the surface may be formed with 5-20 holes, e.g. 7-15 holes. The holes are sized to support a surface tension that blocks flow of a water based liquid.

In some example embodiments, adaptor 351 includes an air inlet 321 that connects to a nebulizer in cartridge 390 and walls 386 are shaped to fit alongside air inlet 321. In some example embodiments, anti-spill cover 380 additionally includes a hollow column or tube 384 that extends from a surface including holes 382 to a rim of walls 386. Column 386 may be configured to collect condensation formed in an aerosol dispensing device during operation with cartridge 390. In some example embodiments, a diameter of a channel formed through column 384 may be between 2-5 mm. Anti-spill cover 380 may be formed from a polymer material, e.g. by injection molding. Optionally, anti-spill cover 380 may be formed with a same polymer material used to form adaptor 351. In some example embodiments, anti-spill cover 380 may be formed as an integral part of adaptor 351, e.g. may not be a separate part.

It is noted that although cartridge 390 is shown to have a cuboid or box shape, other shapes for cartridge 390 are contemplated within the scope of the embodiments described herein.

According to some example embodiments, adaptor 351 includes a nebulizer 323 with Venturi tube configured to impose a Venturi effect. Nebulizer 323 may include an air inlet 321 configured for receiving compressed air, an air outlet 302 through which the air may be expelled in cartridge 390 and suction inlet 324 through which liquid sucked in through a straw 315 enters the Venturi tube, and an aerosol output 304 through which the aerosol is released. Aerosol output 304 may rise out of cartridge 390 through holes 382 and an aerosol dispensing device may direct flow of aerosol output 304. Optionally, the aerosol dispensing device includes a fan that directs and facilitates the dispersion.

Reference is now made to FIG. 9 showing a perspective view of an example anti-spill cover and to FIGS. 10A, 10B, 10C and 10D showing top, side and cross-sectional view of an example anti-spill cover, all in accordance with some example embodiments. Anti-spill cover includes a surface 320 having a plurality of holes 382 with a defined diameter that may support a surface tension of a water based solution housed therein. In some example embodiments, anti-spill cover 380 includes a concave portion 388 that is configured to fit alongside a structure positioned in an outlet 335 of cartridge 390. In some example embodiments, anti-spill cover 380 may also include a rim 311 that may fit around an outlet 335 or within an outlet 335. Optionally, walls 386 may also be formed with holes 382, e.g. adjacent an edge defined between surface 320 and wall 386.

Figure 11A:
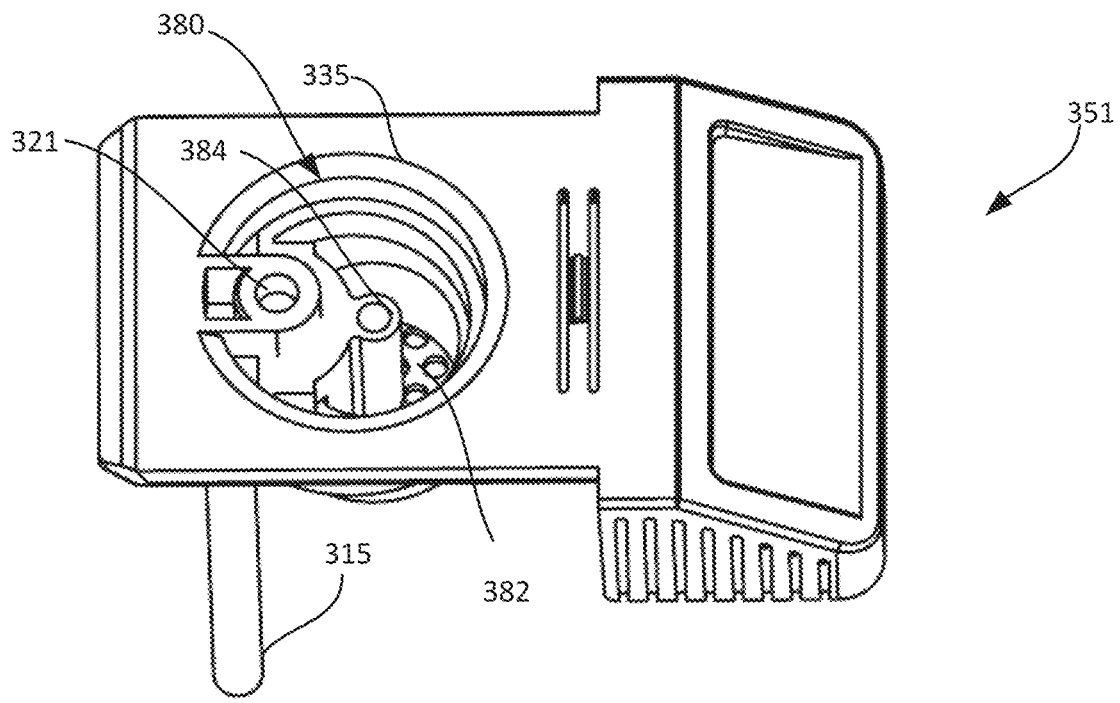
FIGS. 11A and 11B are perspective and side views of an example adaptor configured to be installed on a cartridge in accordance with some example embodiments.
Figure 11B:
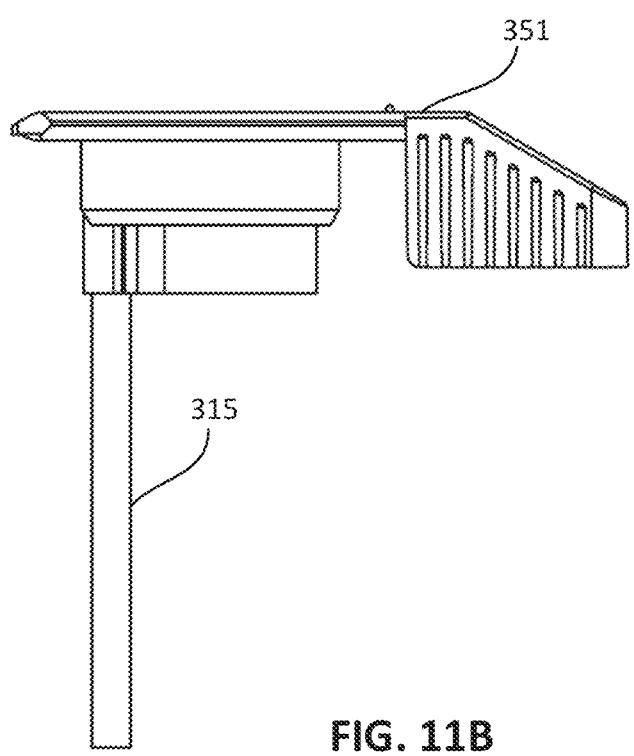
Figure 12:
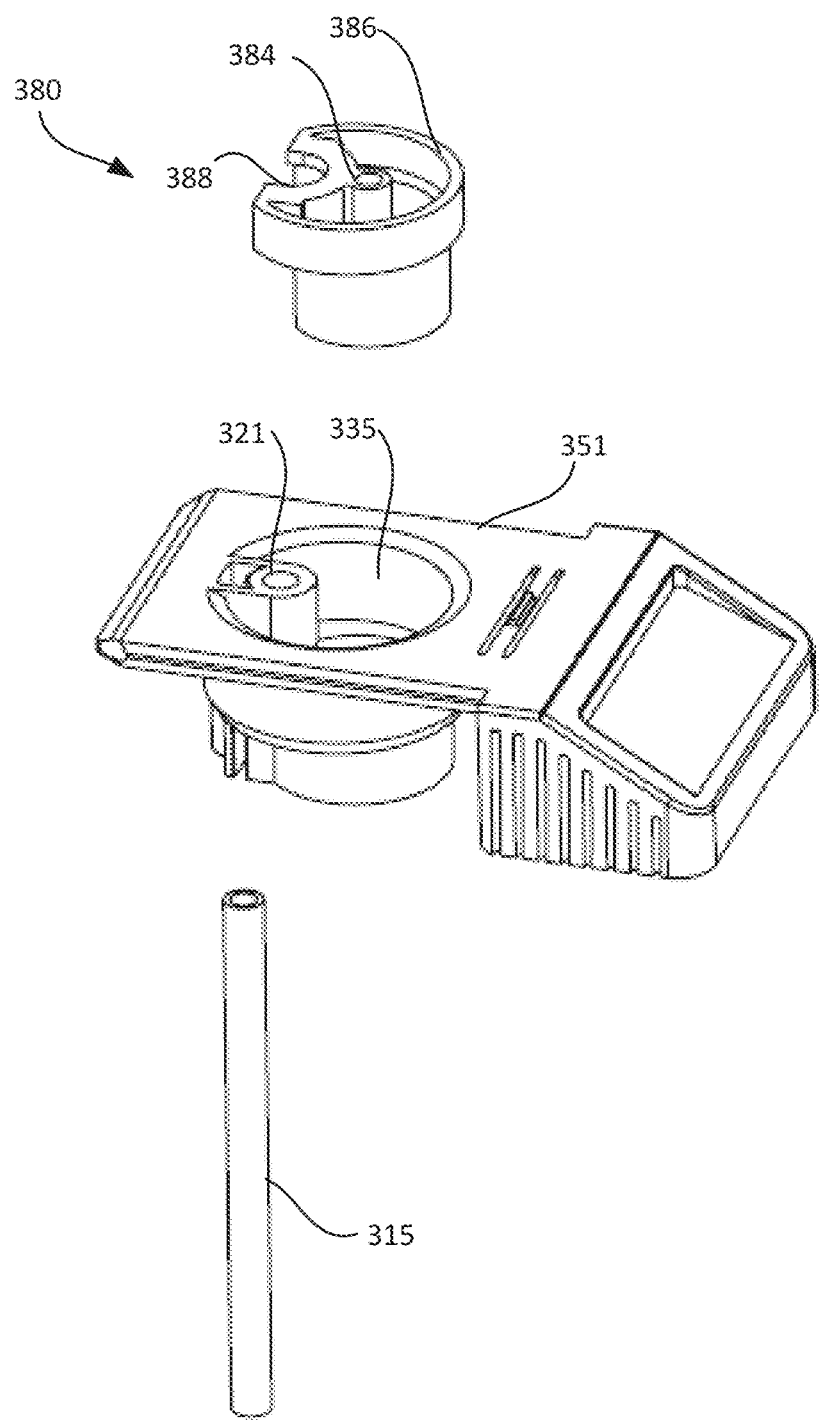
FIG. 12 is an exploded view of an example adaptor configured to be installed on a cartridge in accordance with some example embodiments.

Reference is now made to FIGS. 11A and 11B showing perspective and side views of an example adaptor configured to be installed on a cartridge and to FIG. 12 showing an exploded view of an example adaptor configured to be installed on a cartridge, all in accordance with some example embodiments. In some example embodiments, adaptor 351 may include anti-spill cover 380 integrated therein. In other example embodiments, anti-spill cover 380 may be a separate part that is fitted into outlet 335. Optionally, straw 315 is a separate part that may be fitted onto adaptor 351.

Figure 13A:
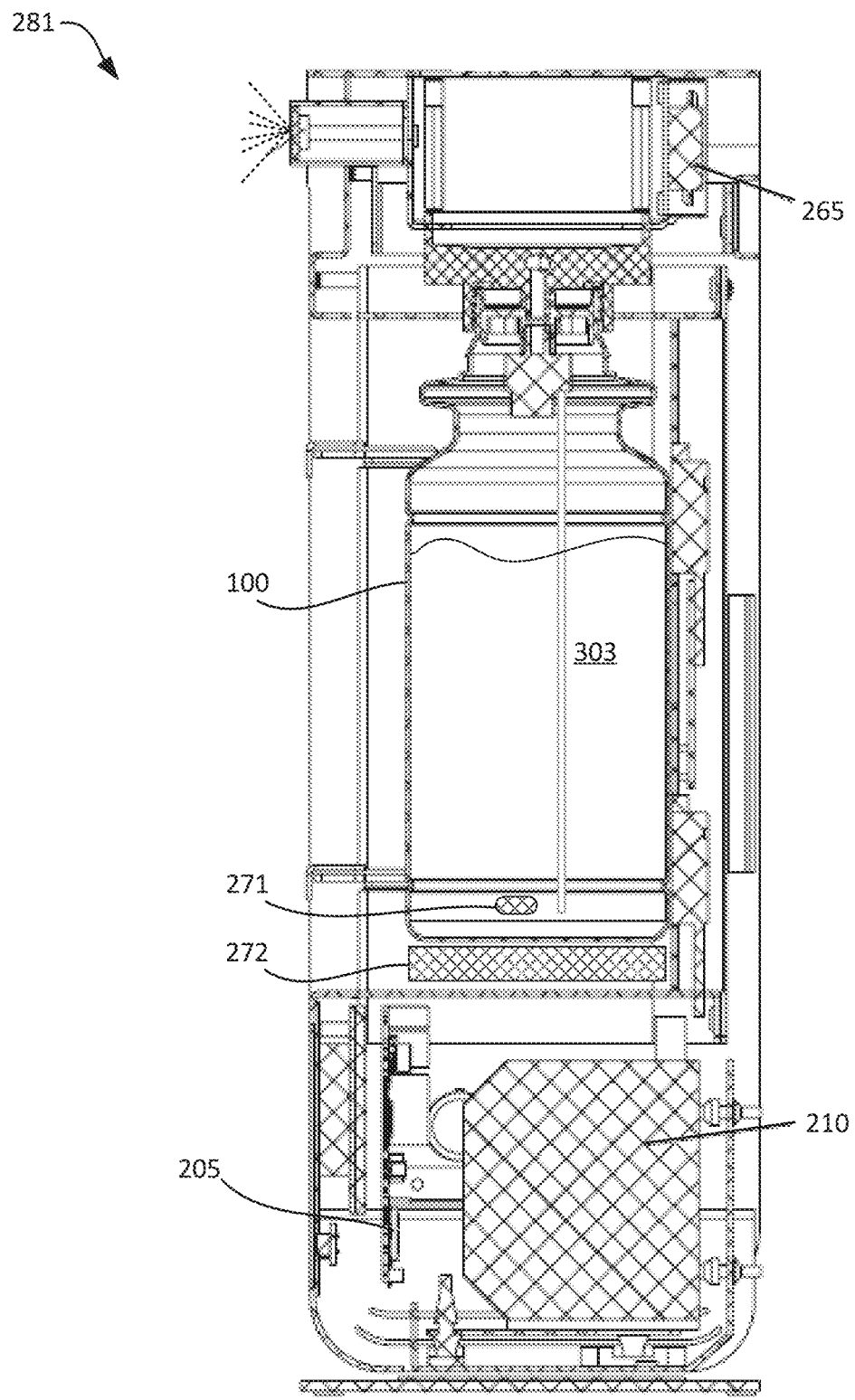
FIGS. 13A, 13B and 13C are simplified schematic cross sectional views of example bottles and aerosol dispensing devices that provide for mixing contents of the bottles, all in accordance with some example embodiments.
Figure 13B:
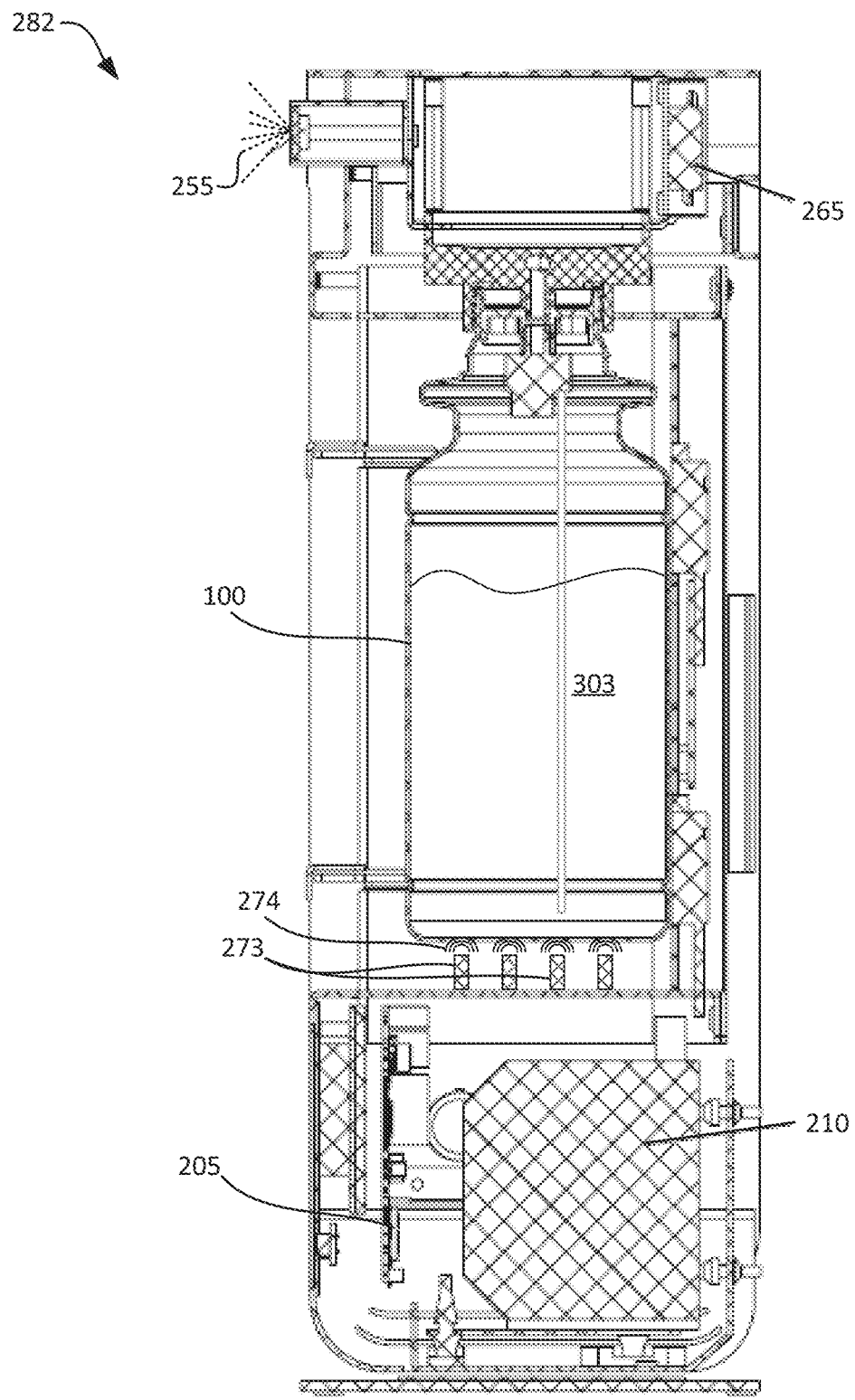
Figure 13C:
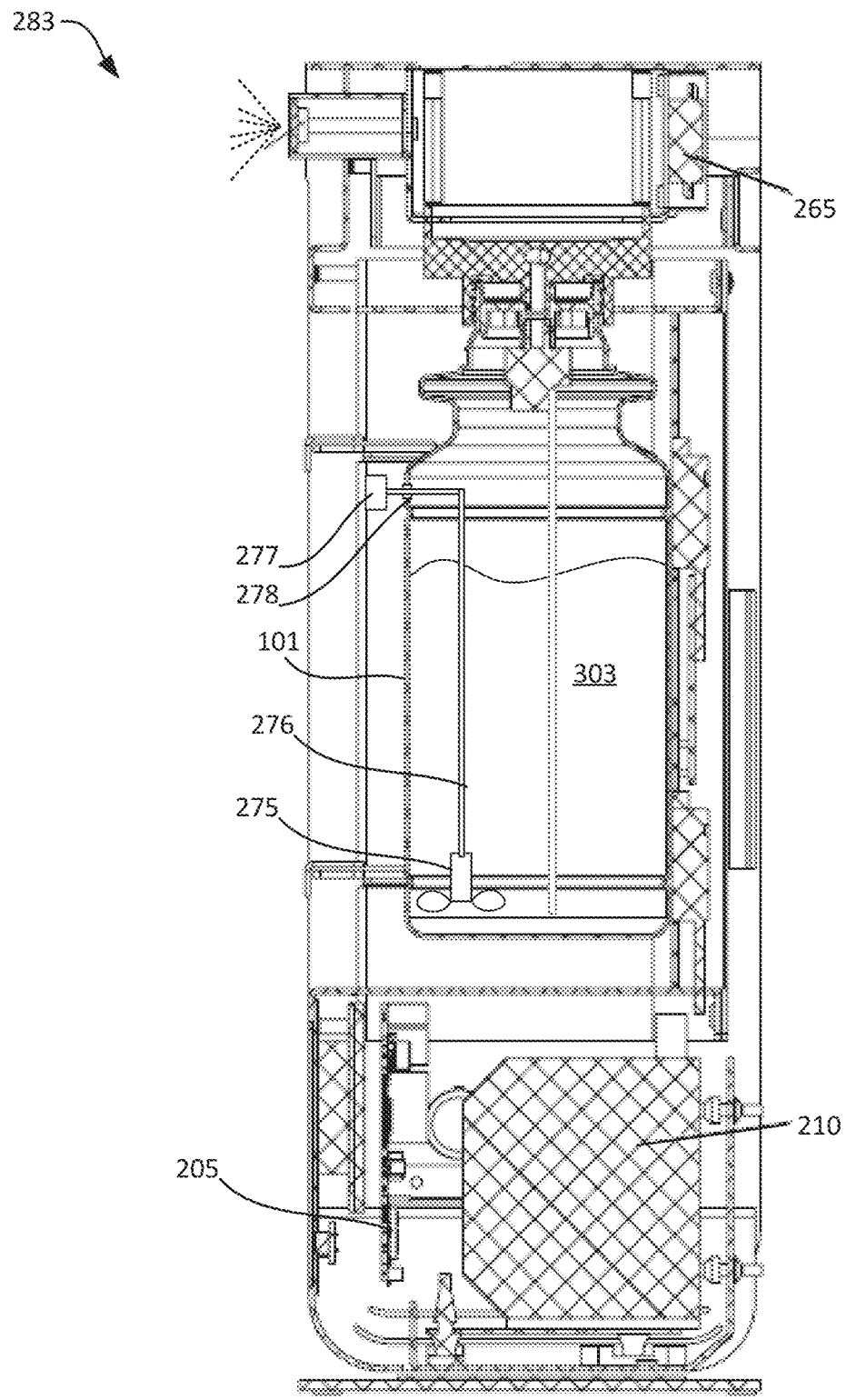

Reference is now made to FIGS. 13A, 13B and 13C showing simplified schematic cross sectional views of example bottles and aerosol dispensing devices that also provide for mixing contents of the bottles, all in accordance with some example embodiments. According to some example embodiments, it is desired to continuously or periodically stir contents of a bottle that is installed in the aerosol dispensing devices to avoid gradients in the bacterial load along a height of the bottle due to settling of the bacteria. By maintaining a substantially same concentration of bacteria, the dosage that is dispensed may be better controlled. Different mechanisms may be applied to introduce stirring in the bottle.

Referring now to FIG. 13A in some example embodiments, bottle 100 may include a stir bar 271 immersed in liquid 303. Stir bar 271 may be induced to spin based on an actuator 272 in example aerosol dispensing device 281 beneath bottle 100. Actuator 272 may for example include a rotating magnet or stationary electromagnets.

Referring now to FIG. 13B in some example embodiments, stirring of liquid 303 may be actuated in an example aerosol dispensing device 282 based on sound waves 274 emitted by one or more micro-speakers 273 that are positioned in aerosol dispensing device 282 around and/or under bottle 100. The sound waves may actuate stirring of liquid 303. Optionally, aerosol the one or more micro-speakers 273 are configured to emit sound waves in the ultrasound range.

Referring now to FIG. 13C, a bottle 101 may be installed with a mechanical stirrer 275 immersed in liquid 303 and aerosol dispensing device 283 may be configured to actuate stirring with mechanical stirrer 275. Optionally, mechanical stirrer 275 includes one or more stirring blades. Optionally, an axle 276 connected to stirrer 275 extends through a dedicated port 278 in bottle 100 and engages a motor 277 while bottle 100 is installed in aerosol dispensing device 283. Motor 277 may turn axle 276 and stirrer 275. Optionally, stirrer 275 is positioned toward the bottom of bottle 101 and port is positioned above height of liquid 303.

Referring now to FIGS. 13A, 13B and 13C, according to some example embodiments, a controller 205 may control be configured to control stirring of liquid 303. Optionally, a sensor may detect settling of the bacterial and stirring rate and frequency may be based on output of sensor. In other examples, mixing may be actuated in coordination with dispensing, e.g. just prior to dispensing. In yet other examples, mixing may be continuous.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. In addition, any priority document(s) of this application is/are hereby incorporated herein by reference in its/their entirety.

What is claimed is:

1. A cartridge comprising:
   a housing configured to house a liquid;
   a collar defining an opening into the cartridge;
   a connector configured to support a nebulizer inside the cartridge, the connector comprising:
      an annular wall;
      a conduit; and
      a plurality of spokes between the annular wall and the conduit;
      wherein the plurality of spokes define openings therebetween and wherein the annular wall is shaped and sized to be fitted into the collar of the cartridge;
   a gasket positioned on the connector, wherein the gasket is configured to provide a sealed connection with a device configured to actuate atomization of the liquid; and
   a nebulizer held within the housing with the connector, wherein the liquid is water based and wherein the nebulizer is configured to atomize the liquid.

2. The cartridge according to claim 1, wherein the nebulizer is positioned to form an aerosol within a volume of the housing.

3. The cartridge according to claim 1, comprising a mechanical stirring element configured to stir the liquid within the housing based on actuation with an external actuator.

4. The cartridge according to claim 3, wherein the mechanical stirring element is a stir bar configured to rotate based applying a rotating magnetic field or a mechanical stirrer including an elongated rod, wherein a distal end of the elongated rod extends outside of the housing and is configured to engage a motor external to the cartridge.

* * * * *